( 12 ) United States Patent
Radicke

(10) Patent No.: US 12,154,751 B2
(45) Date of Patent: Nov. 26, 2024

(54) SYSTEM FOR AT LEAST ONE OF CALIBRATION OR QUALITY CONTROL OF AN FFS X-RAY SYSTEM

(71) Applicant: Siemens Healthcare GmbH, Erlangen (DE)

(72) Inventor: Marcus Radicke, Veitsbronn (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 246 days.

(21) Appl. No.: 17/953,706

(22) Filed: Sep. 27, 2022

(65) Prior Publication Data

US 2023/0097505 A1 Mar. 30, 2023

(30) Foreign Application Priority Data

Sep. 29, 2021 (DE) ...................... 10 2021 210 897.0

(51) Int. Cl.
*H01J 35/14* (2006.01)
*A61B 6/00* (2024.01)
*A61B 6/40* (2024.01)
*A61B 6/58* (2024.01)
*H01J 35/06* (2006.01)
*H01J 35/30* (2006.01)
*H05G 1/52* (2006.01)

(52) U.S. Cl.
CPC .......... *H01J 35/153* (2019.05); *A61B 6/4021* (2013.01); *A61B 6/54* (2013.01); *A61B 6/582* (2013.01); *H01J 35/30* (2013.01); *H05G 1/52* (2013.01); *H01J 35/06* (2013.01)

(58) Field of Classification Search
CPC ....... H01J 35/153; H01J 35/30; A61B 6/4021; H05G 1/52
See application file for complete search history.

(56) References Cited

U.S. PATENT DOCUMENTS

| 2005/0094762 | A1* | 5/2005 | Dunham | .............. A61B 6/4021 |
| | | | | 378/19 |
| 2009/0242744 | A1 | 10/2009 | Erler | |
| 2015/0016589 | A1* | 1/2015 | Melman | ................. A61B 6/487 |
| | | | | 378/62 |
| 2020/0085384 | A1 | 3/2020 | Erler | |

FOREIGN PATENT DOCUMENTS

| DE | 102006032607 A1 | 1/2008 |
| DE | 102018215724 A1 | 3/2020 |

\* cited by examiner

*Primary Examiner* — Chih-Cheng Kao
(74) *Attorney, Agent, or Firm* — Harness, Dickey & Pierce, P.L.C.

(57) ABSTRACT

One or more example embodiments relates to a system for calibration and/or for quality control of an FFS X-ray system, a corresponding FFS X-ray system, a control facility suitable for it and to a method for calibration and/or for quality control of the FFS X-ray system.

20 Claims, 3 Drawing Sheets

SYSTEM FOR AT LEAST ONE OF CALIBRATION OR QUALITY CONTROL OF AN FFS X-RAY SYSTEM

CROSS-REFERENCE TO RELATED APPLICATION(S)

The present application claims priority under 35 U.S.C. § 119 to German Patent Application No. DE 10 2021 210 897.0, filed Sep. 29, 2021, the entire contents of which are incorporated herein by reference.

FIELD

One or more example embodiments of the present invention relates to a system for calibration and/or for quality control of an FFS X-ray system, to a corresponding FFS X-ray system and to a control facility suitable for it and to a method for calibration and/or for quality control of the FFS X-ray system and is preferably suitable for tomosynthesis. In particular, one or more example embodiments of the present invention relates to a calibration method for a magnetic deflection system of an X-ray tube assembly.

BACKGROUND

In tomographic methods of X-ray diagnostics, a method has been used in recent years, which is known by the name "Flying Focal Spot" (FFS). With this method, the electron beam of an X-ray tube assembly issuing from the cathode is deflected by way of a magnetic field, generated for example by a magnetic coil, before it impinges on the anode. The impingement point of the electron beam on the surface of the anode can be changed hereby. FFS is used, inter alia, in mammography.

The principle of FFS can be used to purposefully swivel an X-ray beam over a region or to compensate a locational deviation of an X-ray beam. To be able to achieve a periodic movement of the X-ray beam, the magnetic coil can be subjected to a periodic deflection current. At present, a deflection current is frequently assumed as a periodic function with a period length of, for example, 200 ms (for example as a sawtooth function).

With a rotating X-ray tube assembly, as is used, for example, in the case of tomosynthesis in mammography, FFS has the function, in particular, during the exposure time of an object (for example 40 ms or 70 ms) of compensating the mechanical movement of the X-ray tube assembly in the room by way of an opposed movement of the focal spot, so it appears fixed in position during a projection.

With the FFS method it is possible, in particular, to enable a continuous movement of the X-ray tube without enlarging the effective focal point size of the individual X-ray shots, something which would reduce the spatial resolution.

SUMMARY

One drawback is that the accuracy of the FFS is limited owing to manufacturing tolerances of the FFS deflecting coil and owing to inaccuracies in the mechanical movement of the X-ray tube assembly. Both coil installation and coil winding are subject to a respective manufacturing tolerance, the effect of which is all the greater, the stronger the deflection is due to the coil. The case can also occur, however, where, owing to ageing phenomena or inaccuracies of the acceleration voltage and the movement of the X-ray tube assembly, the FFS deflection changes over time. The quality of the FFS deflection should therefore also be checked at different times, and previously this has not occurred optimally.

One or more example embodiments of the present invention provides an improved method and a corresponding system for calibration and/or or quality control of an X-ray system with which the above-described drawbacks are avoided and in particular the actuation and use of an FFS deflecting coil is optimized.

According to one or more example embodiments, a system for at least one of calibration or quality control of a Flying Focal Spot (FFS) X-ray system, wherein the FFS X-ray system comprises a flat-panel X-ray detector, an X-ray tube assembly with a cathode and an anode and a FFS deflecting coil for FFS deflection of an electron beam between the cathode and the anode in a deflecting direction transverse to a movement of the electron beam. The system includes an absorption mask having an interior and an exterior, wherein the interior and the exterior differ with respect X-ray absorption and the interior being limited at least in the deflecting direction of the electron beam on both sides of the exterior, the absorption mask being positionable in a calibration position through which an X-ray beam radiates from the X-ray tube assembly to the X-ray detector; a measuring facility configured to measure at least one position of a mapping of the absorption mask on the X-ray detector when the X-ray beam is switched on; an allocation unit configured to ascertain a deflection current of the FFS deflecting coil for each measured position of the mapping of the absorption mask on the X-ray detector, and the allocation unit being further configured to create a biunique allocation of the deflection current for the FFS deflection of the electron beam based on each ascertained deflection current and the respectively measured position of the mapping; and a control unit configured for applying a deflection current in the FFS deflecting coil in accordance with at least one of the allocation or for controlling a data stream for storing the allocation for a comparison with earlier allocations.

According to one or more example embodiments, the absorption mask is movable between a rest position outside of an intentional beam cone of the X-ray beam and the calibration position.

According to one or more example embodiments, the absorption mask is at a collimator or in the collimator of the X-ray tube assembly.

According to one or more example embodiments, the absorption mask is at a filter or in the filter of the X-ray tube assembly.

According to one or more example embodiments, the absorption mask is attached to a compression plate for a mammography system.

According to one or more example embodiments, the absorption mask is a phantom, the absorption mask being arranged upstream of a tube output of the X-ray tube assembly.

According to one or more example embodiments, the absorption mask is formed such that an X-ray-absorbing element is in the interior and the exterior is substantially X-ray-transparent, or the interior is X-ray-transparent and the exterior is substantially X-ray-absorbing.

According to one or more example embodiments, an FFS X-ray system includes a flat-panel X-ray detector; an X-ray tube assembly with a cathode and an anode; an FFS deflecting coil for FFS deflection of an electron beam between the cathode and the anode in a deflecting direction transverse to a movement of the electron beam; and a system according to one or more example embodiments.

According to one or more example embodiments, the X-ray tube assembly is an FFS X-ray tube assembly, the FFS X-ray tube assembly including the absorption mask of the system.

According to one or more example embodiments, a control facility for the FFS X-ray system includes the measuring facility; the allocation unit; and the control unit.

According to one or more example embodiments, a method for at least one of calibration or quality control of the FFS X-ray system includes positioning the absorption mask between the X-ray tube assembly and the X-ray detector of the FFS X-ray system such that the X-ray beam from the X-ray tube assembly to the X-ray detector runs through the absorption mask; switching-on the X-ray beam with a pre-defined FFS deflection of the electron beam in the X-ray tube assembly; measuring the position of the mapping of the absorption mask on the X-ray detector when the X-ray beam is switched on and ascertaining the deflection current for the FFS deflection; repeating the measurement for a plurality of different FFS deflections; and creating the biunique allocation of deflection current to FFS deflection of the electron beam, based on the measured plurality of ascertained deflection currents and the respectively measured positions of the mapping.

According to one or more example embodiments, a maximum negative FFS deflection with a maximum negative deflection current and a maximum positive FFS deflection with a maximum positive deflection current are defined.

According to one or more example embodiments, the measuring measures the position of the mapping of the absorption mask at different energies of the X-ray beam.

According to one or more example embodiments, the method further includes tracking the electron beam using the FFS deflection, wherein the deflection current is applied in the FFS deflecting coil in accordance with the created allocation.

According to one or more example embodiments, the method further includes creating at least one further allocation at different positions of the X-ray tube assembly.

BRIEF DESCRIPTION OF THE DRAWINGS

One or more example embodiments will be described in more detail with reference to the accompanying figures. Identical components are provided with identical reference numerals in the different figures. As a rule, the figures are not to scale. In the drawings.

DETAILED DESCRIPTION

Figure 1:
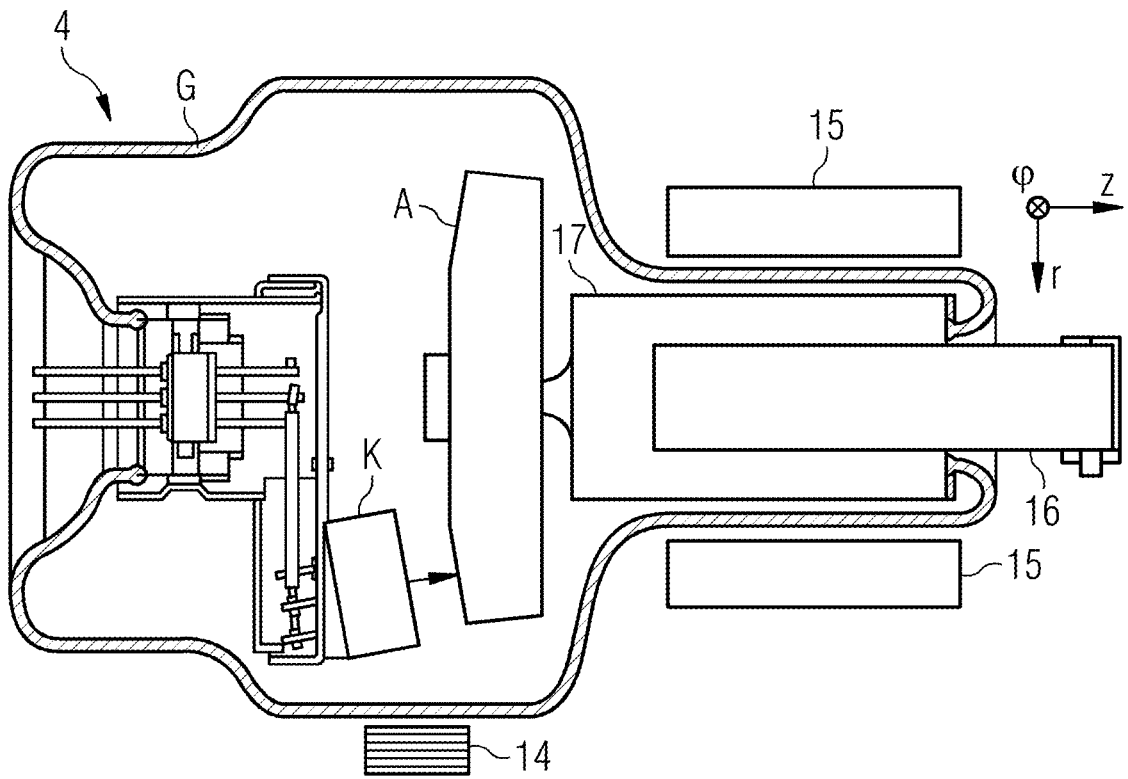
FIG. 1 shows a schematic representation of an FFS X-ray tube assembly with a rotary anode in accordance with the prior art.

The inventive method serves for calibration and/or for quality control of an FFS X-ray system (in other words, an X-ray system with a "Flying Focal Spot"). An X-ray system of this kind is known in principle to a person skilled in the art and apart from an X-ray tube assembly, comprises an X-ray detector for detection of the radiation issuing from the X-ray tube assembly and an FFS deflecting coil for deflecting the electron beam in a deflecting direction. The X-ray tube assembly is preferably an FFS X-ray tube assembly, which as a functional element comprises a cathode, an anode and additionally the FFS deflecting coil. The FFS deflecting coil can be arranged inside or outside the vacuum housing (the X-ray tube) of the X-ray tube assembly.

As far as the deflecting direction is concerned, a positive FFS deflection (in one direction) and a negative FFS deflection (in the other direction) is intended thereby. If a current flows through the FFS deflecting coil, it thus induces a magnetic field, and the electron beam is deflected in accordance with the Lorentz force (transverse to its direction of movement). With a positive current, the FFS deflection takes place in the one direction, with a negative current (reverse polarity), the FFS deflection takes place in the opposite direction.

The method comprises the following components:

an absorption mask with an interior and an exterior, wherein interior and exterior differ in respect of their X-ray absorption and the interior is limited at least in the deflecting direction of the electron beam on both sides of the exterior, and wherein the absorption mask is located in a calibration position, through which an X-ray beam intentionally radiates from the X-ray tube assembly to the X-ray detector, or can be positioned there at least intentionally, a measuring facility configured for measuring a position of a mapping of the absorption mask on the X-ray detector when an X-ray beam is switched on, an allocation unit configured for ascertaining a deflection current of the FFS deflecting coil for a measured position of the mapping of the absorption mask on the X-ray detector, and creating a biunique allocation of deflection current for the FFS deflection of the electron beam based on a plurality of ascertained deflection currents and the respectively measured positions of the mapping, a control unit configured for applying a deflection current in the FFS deflecting coil in accordance with the allocation and/or for controlling a data stream for storing the allocation for a comparison with earlier allocations.

With regard to the absorption mask (hereinafter also called a "mask" for short), there is a large number of possible forms. It should be common to all of these forms, however, that it is possible to clearly identify a deflection of their mapping on the X-ray detector (for a better overview, solely a "detector" will also be mentioned hereinafter). This is achieved in that a central region (interior), for example a hole or a slit, but also an absorbent point or a wire, differs from the adjoining regions (exterior) to the right and left (in the deflecting direction) in respect of the X-ray absorption. One example would be a wire (interior), which is surrounded by air (exterior) and is held only at two points, or a hole (interior) in a lead plate (exterior). Since the mapping of the mask in the case of an FFS deflection of the electron beam moves only in one direction on the detector, it is also only necessary for interior and exterior to be clearly separable in this direction of movement (deflecting direction). It is nevertheless preferred, however, that the exterior substantially completely surrounds the interior. The expression "substantially" means in this regard that the interior is surrounded to more than 90° by the exterior, preferably to more than 95%. Purely functionally it may be stated that "substantially" means that only necessary holding structures should be present for the interior, for example for holding a wire.

The calibration position is the position in which the absorption mask should be located for a calibration. This calibration position lies where the X-ray beam is also located during a scan. The preferred calibration position is, at least in respect of the deflecting direction, substantially in the center of the X-ray beam, with this meaning that the calibration position should be located in the center of the used part of the beam cone, viewed at least from the deflecting direction, since this is the most important direction for the measurement. Here the expression "substantially" preferably means that a deviation from the center point is preferably less than 10% of the distance from the center point to the edge of the used part of the beam cone, particularly preferably less than 5%. In principle, the calibration position can also be asymmetrical, however, in other words lie at the end of the X-ray beam cone, in particular in respect of a direction orthogonal to the deflecting direction since this orthogonal direction is not as important for the measurement.

The mask can already be in the calibration position but should be removed for an examination of a patient. It can, however, also be positioned there only intentionally, and this means that it is formed such that it can be detachably arranged in the calibration position or can be moved to this location by a movement mechanism.

If an X-ray beam is now switched on, a mapping of the mask can be seen on the X-ray detector when a mask is positioned in the calibration position. With an FFS deflection of the electron beam, the mapping "wanders" over the detector and the interior can clearly be identified against the exterior.

The measuring facility is preferably configured for an automatic measurement or a digital evaluation of the X-ray image. Nowadays a detector is usually designed as a digitally measuring semiconductor detector, so an acquired image of the detector can be digitally processed. The mapping of the mask can easily be automatically segmented on the otherwise homogeneously illuminated image and the position thereof on the detector easily ascertained owing to the image position of the mapping. It is preferred that an image position without FFS deflection of the electron beam is assumed as an "original position" or "zero" and measured positions are disclosed relative to this original position.

In addition to the position of the mapping, the deflection current is also ascertained with which the electron beam is deflected in the context of the FFS during the measurement.

With the ascertained deflection current and the position of the mapping (in particular in the form of a spacing from the original position), the allocation unit can now calculate how large the FFS deflection of the electron beam was. If the mask is arranged on the anode at a distance X from the focal point of the electron beam and the detector was to have the spacing Y from this focal point, then $F = A \cdot X/Y$ results from a deflection A of the mapping of the mask on the detector for the FFS deflection F of the electron beam. For a small error, the mask should be located as close as possible to the focal point since A can be affected by a measuring error.

If in each case the FFS deflection of the electron beam is now ascertained for a plurality of measurements and the respective deflection current measured, these two variables can be allocated to each other in the allocation. Due to the manufacturing tolerances mentioned above, this allocation can differ from a proportional allocation, at least in regions with a large deflection. The allocation will always be biunique, however, since with a (in terms of amount) greater current, a (in terms of amount) greater FFS deflection also always occurs.

The allocation can be created in the form of a (look-up) table or in the form of a mathematical function. For the latter, a function (for example a polynomial) can be fitted to the individual measuring points.

The real FFS deflection of the electron beam (and therewith the position of the focal point on the anode) is determined in the case of calibration with a predefined deflection current. For a subsequent measurement, information about the deflection current to be applied for a predefined FFS deflection is required, however. It is precisely this information that the allocation created via the allocation unit supplies.

Via the control unit, which can by all means be part of a control facility of the FFS X-ray system, the deflection current ascertained from the allocation can then be applied for a desired FFS deflection.

A plurality of allocations should be acquired at different times for quality control. For this purpose, the control unit is alternatively or additionally configured for controlling a data stream for storing the allocation for a comparison with earlier allocations. In principle, the storage alone suffices for this since allocations, which have been created at different times, can be manually compared with each other in this way. The control unit is particularly preferably also configured for an automatic comparison of these allocations (from measurements at different times), however, and in particular additionally configured to carry out a calibration for compensation of time-related deviations. Deviations in the quality can be directly and automatically calibrated thereby.

An inventive FFS X-ray system comprises a flat-panel X-ray detector, an X-ray tube assembly with a cathode and an anode, an FFS deflecting coil for FFS deflection of an electron beam between cathode and anode in a deflecting direction transverse to a movement of the electron beam and an inventive system. It is preferred in this connection that the X-ray tube assembly is configured as an FFS X-ray tube assembly, and this means that the FFS deflecting coil is part of the X-ray tube assembly.

An inventive control facility for an FFS X-ray system comprises the following components:
  a measuring facility configured for measuring the position of a mapping of the absorption mask the X-ray detector,
  an allocation unit configured for ascertaining in each case a deflection current of the FFS deflecting coil for a plurality of measured positions of the mapping of the absorption mask on the X-ray detector, and creating a biunique allocation of deflection current to FFS deflection of the electron beam based on the deflection currents and the measured positions of the mapping,
  a control unit configured for applying a deflection current in the FFS deflecting coil in accordance with the allocation and/or for controlling a data stream for storing the allocation for a comparison with earlier allocations.

It does not comprise a mask. If an FFS X-ray system comprises a mask it becomes an inventive FFS X-ray system due to the inventive control facility. In principle, only an X-ray detector, an FFS X-ray tube assembly, the mask and the control facility are required for constructing an inventive FFS X-ray system.

An inventive method for calibration and/or for quality control of an inventive FFS X-ray system comprises the following steps:

- positioning the absorption mask between the X-ray tube assembly and the X-ray detector of the FFS X-ray system in such a manner that an X-ray beam from the X-ray tube assembly to the X-ray detector would run through the absorption mask,
- switching-on the X-ray beam with a predefined FFS deflection of an electron beam in the X-ray tube assembly,
- measurement of the position of a mapping of the absorption mask on the X-ray detector when the X-ray beam is switched on and ascertaining the deflection current for the FFS deflection,
- repetition of the measurement for a plurality of different FFS deflections,
- creation of a biunique allocation of deflection current to FFS deflection of the electron beam, based on the measured plurality of ascertained deflection currents and the respective measured positions of the mapping.

As already stated above, for calibration or for quality control, the mask has to be located in the calibration position, in other words between the X-ray tube assembly and the X-ray detector, so it conceals part of the X-ray beam (in particular its center).

With a predefined FFS deflection of the electron beam, the X-ray beam is now switched on for a measurement and illuminates the mask. A mapping of the mask is produced on the detector.

The measurement has already been described above. The position of the mapping and, in particular, a measure of the deflection of the mapping from an original position is obtained already. In addition, the deflection current is ascertained for the allocation (also by way of the allocation unit. It is pointed out at this point that the deflection current can be ascertained by a separate measuring device, which is ascribed to the allocation unit in the context of one or more example embodiments of the present invention, however. In most cases, the deflection current is predefined by the system, however, so the relevant data can be easily retrieved. It is preferred, where available, to access this data or to use predefined information relating to the deflection current for ascertaining the deflection current.

The measurement is now repeated several times for different FFS deflections for generating numerous measuring points for the allocation. In this case, for example the deflection current is passed through from a maximum negative value above zero (current switched off, no FFS deflection) up to a maximum positive value in the form of discrete FFS deflections per measurement. It is also possible, however, to continuously pass through a predefined range for the deflection current and to (quickly) carry out numerous measurements consecutively.

Preferably, measurements are carried out with both increasing current strength as well as with decreasing current strength. While the FFS deflecting coil is in most cases an air coil, so in this case an hysteresis should develop only weakly, if at all, metal components of the X-ray tube assembly could result in an hysteresis. In this case, an individual biunique allocation would be obtained in each case for an increasing deflection current and a decreasing deflection current. In general, it is preferred if a measurement is carried out with a characteristic curve of the deflection current as would also be applied in the case of a real examination, for example a tomosynthesis measurement, in other words in the form of a sawtooth for example. An increase or a decrease in the current preferably occurs more slowly than in the case of the real examination, so a sufficient number of measuring points can be measured.

The creation of the allocation has likewise already been described above. The more measured values there are available, the more accurate the allocation. Measurements can by all means be made several times with the same FFS deflections (or an FFS deflection range with a plurality of measurements passed through) in order to make statistical deviations manageable.

The resulting allocation can be, for example, an allocation table (look-up table) or an allocation graph or an allocation function.

Owing to the projection of the mapping of the mask on the detector, the mode of operation of the FFS can be tested in a manner individual to the system and a system can be automatically calibrated via the allocation.

Further, particularly advantageous embodiments and developments of one or more example embodiments of the present invention can be found in the dependent claims and the following description, with it being possible for the claims of one category also to be developed analogously to the claims and parts of the description relating to another category of claims and, in particular, individual features of different exemplary embodiments or variants can also be combined to form new exemplary embodiments or variants.

In accordance with a preferred system, the absorption mask is movable, so it can be moved back and forth between a rest position outside of an intentional beam cone of the X-ray beam and the calibration position. A mechanical movement is meant thereby and not manual removal and conveying to another location (although this is generally also possible). The mechanical movement can by all means take place manually, for example by moving a lever or turning a wheel, but is preferably automated. For this, it is preferred that the system comprises a movement unit configured for motorized (and in particular also for automated) movement of the absorption mask between rest position and calibration position.

In accordance with a preferred system, the absorption mask is arranged at or in a collimator of the X-ray tube assembly, in particular (at least in respect of the deflecting direction) substantially in the center point of the collimator (here, that which was stated above in relation to "substantially" in respect of a positioning in an X-ray beam applies since the collimator defines the utilizable X-ray cone). An "adjustment collimator" of this kind can be installed, for example, during the course of manufacture of the X-ray system or by service engineers.

In accordance with a preferred system, the absorption mask is arranged at or in a filter of the X-ray tube assembly. The filter can by all means be present in the collimator or together with the collimator. A preferred position is (at least in respect of the deflecting direction) substantially in the center of the filter (see the preceding statements relating to the expression "substantially" in this regard). In particular a mirror can be used as a filter for visual monitoring of a field of view, to which mirror the absorption mask is attached. For example, the collimator contains a filter which has an individual point (alternatively, a dedicated structure) as a mask, for example (at least in respect of the deflecting direction) in the center of the filter. Ideally, no specific adjustment collimator has to be installed, instead a corresponding calibration filter could be present in each X-ray system. It would be particularly practical in this case if the currently installed mirror is slightly X-ray-transparent, and a point absorber is provided downstream of the mirror.

In accordance with a preferred system, at least one absorption mask is attached in, on or at a compression plate for a mammography system. This location can be used as an alternative or in addition to the positions described previously. The compression plate preferably comprises an identification feature, for example an electronic identification feature (for example an RFID chip) or visible identification feature (for example a barcode or QR code). The compression plate can be identified by the FFS X-ray system by way of the identification feature, and this is already prior art. A calibration in accordance with the inventive method can now be automatically initiated, however, as soon as this particular compression plate has been identified by the FFS X-ray system.

It should be noted in this regard that preferably the inventive method can also be automatically initiated if the mask is located in the calibration position. For this, the FFS X-ray system can be configured such that it automatically identifies when the absorption mask is located in the calibration position and on identification, automatically initiates the inventive method.

In accordance with a preferred system, the absorption mask is a phantom, which is arranged or can be attached upstream of a tube output of the X-ray tube assembly. The phantom is preferably arranged inside a cover of the X-ray tube assembly in such a way that it can be moved in a motorized manner from the rest position into the calibration position and back. It can also simply be manually attached outside of the cover, however, although this constitutes a slightly increased potential for error.

In accordance with a preferred system, the absorption mask is formed such that an X-ray-absorbing element is arranged in the interior and the exterior is substantially X-ray-transparent, wherein the element is preferably a disk or a wire.

In accordance with an alternative preferred system, the mask is formed such that the interior is X-ray-transparent and the exterior is substantially X-ray-absorbing, wherein the interior is preferably a hole or a slit. Exterior or interior are therefore very different in respect of their X-ray transmission or absorption. Preferably, the exterior substantially surrounds the interior.

It is preferred that the X-ray tube assembly additionally comprises a collimator and the absorption mask is arranged at or in the collimator. Alternatively or in addition, it is preferred that the X-ray tube assembly additionally comprises a filter and the absorption mask is arranged at or in the filter. This filter can by all means be arranged in a collimator. A mirror can particularly preferably be used as a filter, which mirror is used for visual representations of the X-ray field. An arrangement of the mask substantially in the center of the respective element (at least in respect of the deflecting direction) is particularly preferred.

In accordance with a preferred method, a maximum negative FFS deflection with a maximum negative deflection current and a maximum positive FFS deflection with a maximum positive deflection current is defined. For the measurements, FFS deflections are then set at or between the maximum FFS deflections. It is preferred that for this, measurements are carried out with maximum positive deflection current and/or with maximum negative deflection current and/or with switched-off deflection current. Measuring points with large deflections are particularly preferred since manufacturing tolerances make themselves particularly disruptively noticeable in this case. It is particularly preferred in this regard that more measuring points are produced with smaller changes in the FFS deflections the greater the value of the deflection current is. The allocation is thus increasingly more refined with larger FFS deflections.

In accordance with a preferred method, measurements are carried out at different energies of the X-ray beam, in other words, at a higher energy of the electron beam or at a higher tube voltage. This means that for different energies, in each case individual allocations are produced with the inventive method. Influences of the energy on the FFS deflection can be identified and compensated in this way. Accordingly, only the suitable allocation for calibration or for quality control have to be used in the case of a measurement with a predefined energy.

In accordance with a preferred method, for an examination, in which the electron beam is to be tracked by way of an FFS deflection, for a predefined FFS deflection, a deflection current in accordance with the created allocation is applied in the FFS deflecting coil. If the method served until now only for creating an allocation, which can be used for calibration or for quality control, this embodiment serves to now use the allocation automatically for a calibration. It should be noted that in this regard that the calibration cannot be applied, or can only applied with difficulty, during an examination since the mask is located in the X-ray beam. It is preferred therefore that the allocation is created outside of an examination and exists in a stored state. If an examination is now pending, the suitable allocation is selected (for example in accordance with the energy used) and used for calibration or for quality control.

In accordance with a preferred method, additionally with positioned mask, at least one further allocation is created at different positions of the X-ray tube assembly. It should be noted in this regard that previously it was particularly advantageous if the X-ray tube assembly rested relative to the detector in order to calibrate the procedure of the FFS. Deviations in the perfect circular path and a tilting of the X-ray tube assembly can be calibrated by way of the possibility now presented (second measurement with moved X-ray tube assembly).

The preferred method comprises the following steps:
switching on the X-ray beam at a predefined position of the X-ray tube assembly,
measuring the position of a mapping of the absorption mask on the X-ray detector when the X-ray beam is switched on,
repeating the measurement for a plurality of different positions of the X-ray tube assembly,
creating the further allocation of the position of the mapping and the position of the X-ray tube assembly with the allocation unit, based on the measured plurality of ascertained deflection currents and the respectively measured positions of the mapping.

In principle, this preferred method is carried out in a manner corresponding to the method for calibration and/or for quality control of the FFS deflection, wherein now, instead of an FFS deflection, the X-ray tube assembly is moved.

Particularly preferably, however, in each case an individual allocation of deflection current and FFS deflection of the electron beam is created for a plurality of discrete positions of the X-ray tube assembly. This means that an optimum FFS deflection (optimum selection of the deflection current) can be achieved at different positions of the X-ray tube assembly.

A movement of the X-ray tube assembly together with an FFS deflection is particularly preferred in this regard. The calibration can be accurately validated thereby and a good possibility of quality control is thus obtained.

In accordance with a preferred method, the pulse time for an X-ray projection during an examination is set such that the FFS deflection is less than 80%, in particular less than 60%, of the maximum possible FFS deflection. Particularly preferably, the control unit is configured such that only this smaller region of the FFS deflection is used. The edge regions more susceptible to errors are thus omitted.

Figure 2:
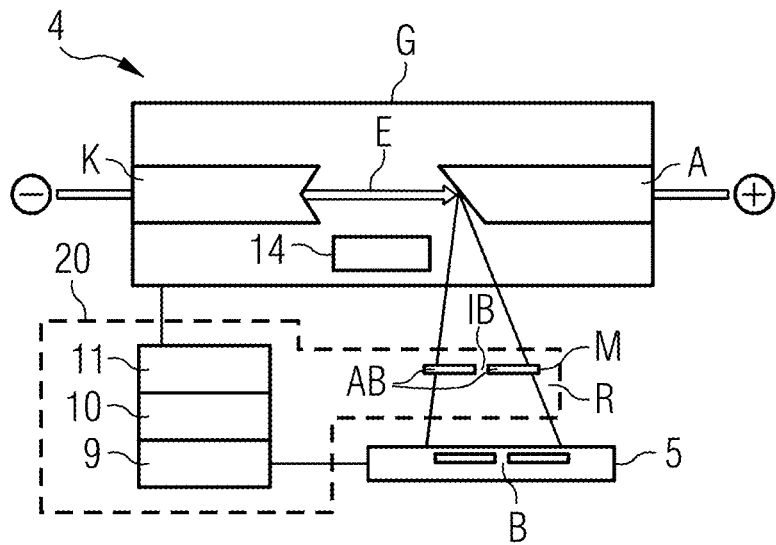
FIG. 2 shows a schematic representation of a preferred exemplary embodiment of a system in a side view.

FIG. 2 shows a schematic representation of an X-ray tube assembly 4 with a rotary anode in accordance with the prior art. Arranged in an evacuated housing G (of the actual X-ray tube) are a cathode K and an anode A, between which, during operation of the X-ray tube assembly 4, an electron beam E is accelerated and impinges on the anode A.

So the impingement point of the electron beam E on the anode A can be changed, an FFS deflecting coil 14 is arranged between cathode K and anode A, the effect of which is an FFS deflection of the electron beam E. If it is subjected to a deflection current IS (see for example FIG. 8), it generates a magnetic field in which the electron beam E is deflected. The deflection takes place here as a function of the polarity of the deflection current either into the image plane or out of it.

While the X-ray tube assembly is being moved on a circular path in direction φ, and an X-ray beam R (see FIG. 2) is being irradiated in direction r, the electron beam E can be deflected in the φ-direction or regulated with the FFS deflecting coil 14. The directions are represented on the right at the edge, wherein it should be noted that this is a cylindrical coordinate system. With this X-ray tube assembly 4, the anode A is rotated via a rotary anode drive 15 on the rotor 17 about its bearing 16 (as stator 16).

Figure 4:
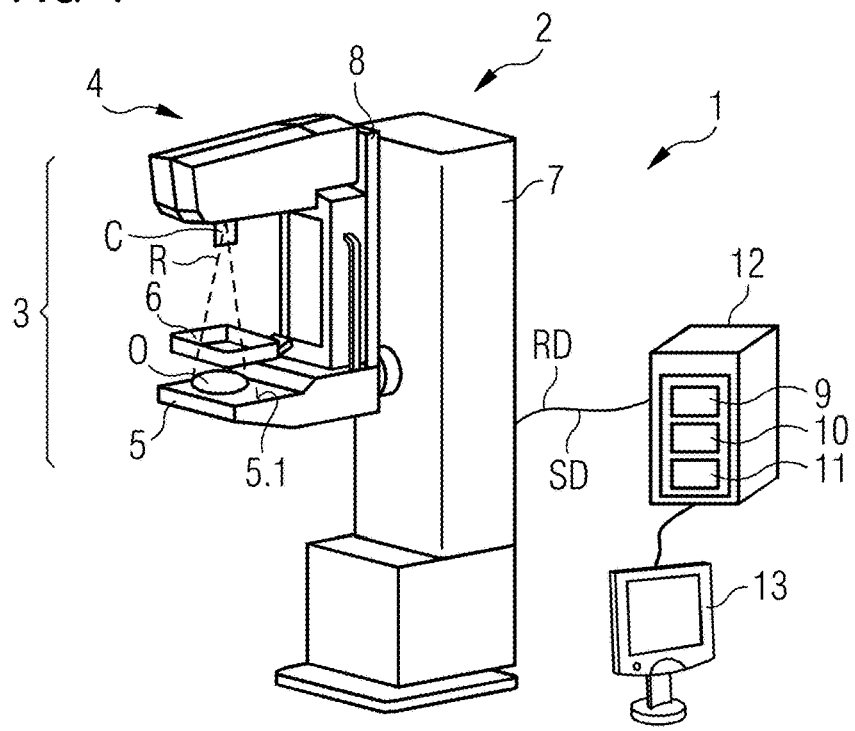
FIG. 4 shows a roughly schematic representation of a preferred tomosynthesis system with a preferred system according to an example embodiment.

FIG. 2 shows a simplified example of an X-ray tube assembly 4 with an inventive system 20 for calibration and/or for quality control of an FFS X-ray system 1 (see for example FIG. 4). For example an X-ray tube assembly 4 as in FIG. 1 can be used as the X-ray tube assembly 4.

The X-ray tube assembly 4 irradiates an X-ray beam R onto a flat-panel X-ray detector 5, it being possible for the electron beam E to be deflected in the X-ray tube assembly 4 via the FFS deflecting coil 14. This deflection takes place into the image plane and out of the image plane.

Figure 3:
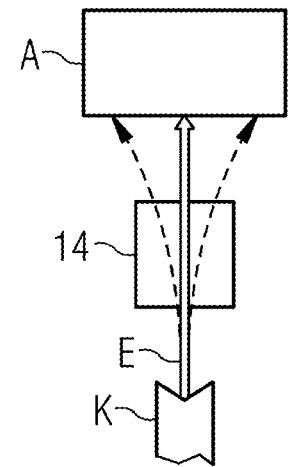
FIG. 3 shows a detail of FIG. 1 in plan view.

The plan view in FIG. 3 represents the deflection of the electron beam E in this X-ray tube assembly 4.

The system 20 comprises an absorption mask M, a measuring facility 9, an allocation unit 10 and a control unit 11.

The absorption mask M has an interior IB and an exterior AB, with interior IB and exterior AB differing in respect of their X-ray absorption and the interior IB being delimited, at least in the deflecting direction of the electron beam E, on both sides from the exterior AB. This delimitation is not represented here since the deflecting direction projects out of the image plane. A corresponding demarcation orthogonal to the deflecting direction is represented, however. In this case, an X-ray-transparent hole as the interior IB is completely surrounded in the exterior AB by an X-ray-absorbing material, therefore.

The absorption mask M is located in a calibration position P (see FIG. 7) through which the X-ray beam R intentionally radiates from the X-ray tube assembly 4 to the X-ray detector 5.

The measuring facility 9 serves for measuring a position of a mapping B of the absorption mask M on the X-ray detector 5 when an X-ray beam R is switched on. It can directly access the data of the detector 5 and determine the position of the mapping B on the detector here. The simplicity can be imagined that with no FFS deflection, the zero point is located and a position of the mapping B in the case of an FFS deflection is given as the distance from the zero point.

Figure 7:
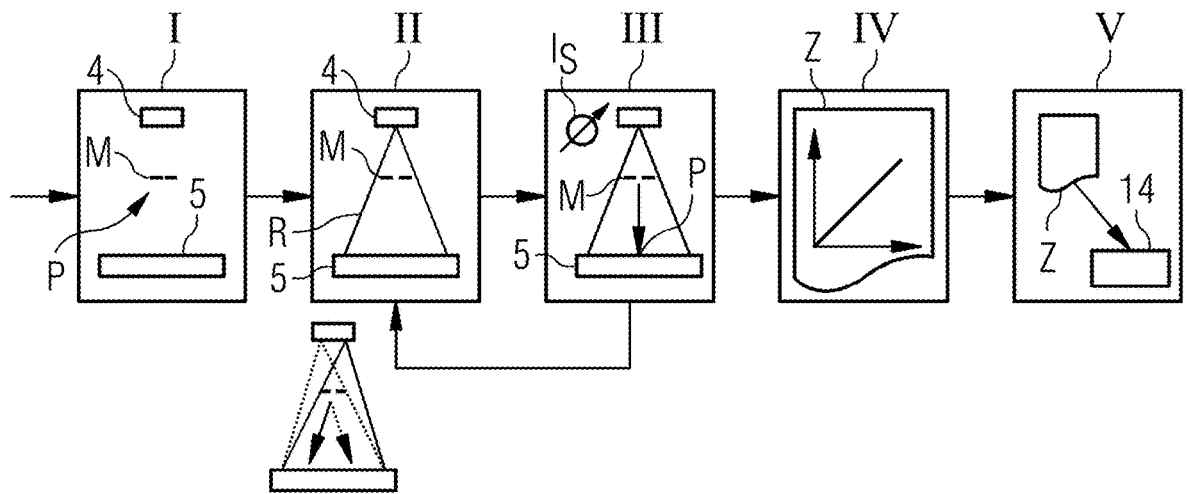
FIG. 7 shows a sequence plan for one possible sequence of an inventive method according to an example embodiment.

The allocation unit 10 serves for ascertaining the deflection current IS of the FFS deflecting coil 4 for a measured position of the mapping B of the absorption mask M on the X-ray detector 5. It serves, moreover, for creating a biunique allocation Z of deflection current IS and FFS deflection of the electron beam E based on a plurality of ascertained deflection currents IS and the respective measured positions of the mapping B. FIG. 7 represents in more detail how this occurs.

The control unit 11 is used for applying a deflection current IS in the FFS deflecting coil 14 in accordance with the allocation Z.

FIG. 4 shows, by way of example, and roughly schematically a tomosynthesis system 1. Relative directional information, such as "above", "below", etc. refer to a tomosynthesis system 1 intentionally set up for operation. The tomosynthesis system 1 comprises a tomosynthesis device 2 and a control facility 12. The tomosynthesis device 2 has a column 7 and a source-detector arrangement 3, which, in turn, comprise an X-ray tube assembly 4 and a detector 5 with a detector panel 5.1. The column 7 stands on the ground during operation. The source-detector arrangement 3 is slidably connected to it, so the height of the detector panel 5.1, the spacing from the ground therefore, can be set to the chest height of a female patient.

A breast O of the female patient (represented schematically here) rests as an examination object O for an examination on the upper side of the detector panel 5.1. A plate 6 is arranged over the breast O and the detector panel 5.1 and is slidably connected to the source-detector arrangement 3. For the examination, the breast O is compressed and simultaneously fixed in that the plate 6 is lowered onto it, so a pressure is exerted on the breast O between plate 6 and detector panel 5.1.

The X-ray tube assembly 4 is arranged opposite the detector 5 and designed such that the detector 5 detects X-ray radiation R emitted by it once at least some of the X-ray radiation R has penetrated the breast O of the female patient. The X-ray tube assembly 4 can be swiveled relative to the detector 5 via a rotary arm 8 in a range of ±50° about a basic setting in which it is perpendicular above the detector panel 5.1. The detail to be acquired can be specified or limited via a collimator C, which can also contain filter C.

The control facility 12 receives the raw data RD of the measurement and sends control data SD to the tomosynthesis device 2 via a data interface. It is connected to a terminal 13 via which a user can communicate commands to the tomosynthesis system 1 or retrieve measurement results. The control facility 12 can be arranged in the same room as the tomosynthesis device 2, but it can also be located in an adjoining control room or even further away.

The inventive system 20 (see FIG. 3) is in this case part of the control facility 12.

Figure 5:
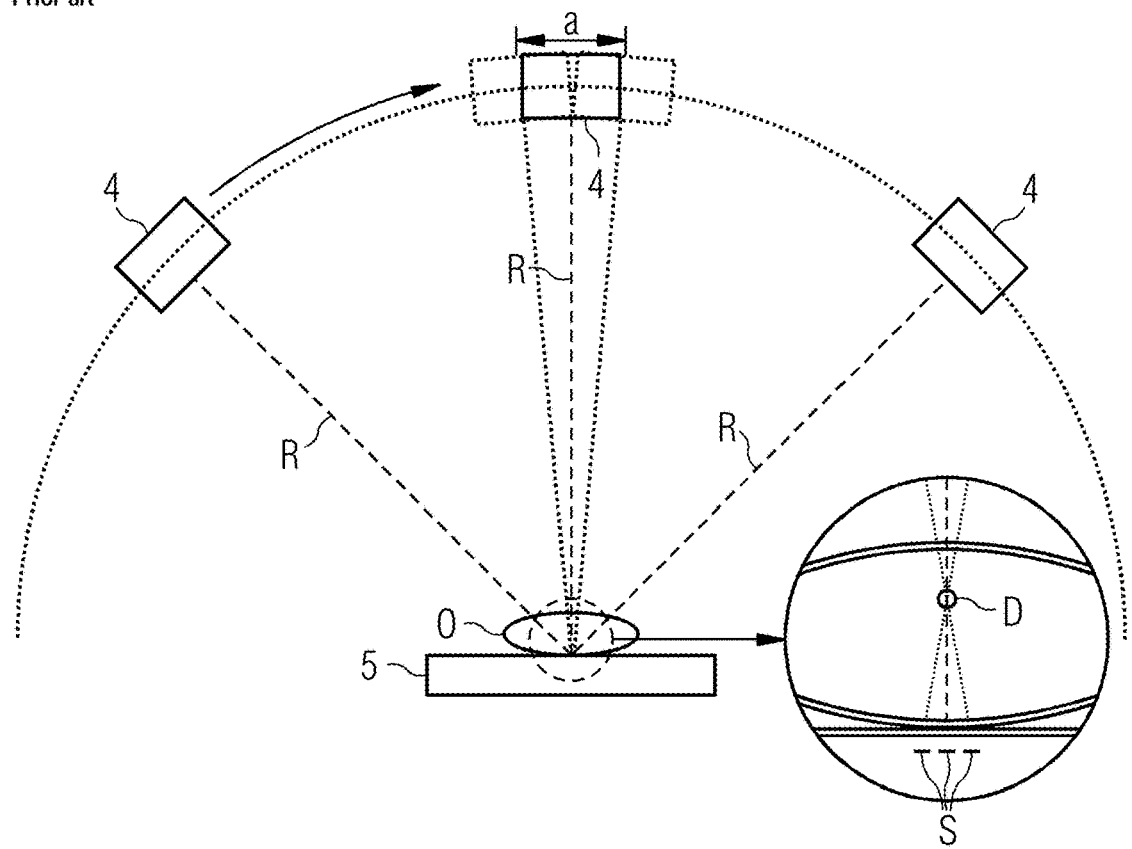
FIG. 5 shows the movement of an X-ray tube assembly during a tomosynthesis examination in accordance with the prior art.

FIG. 5 shows the movement of an X-ray tube assembly 4 of an FFS X-ray system as in FIG. 1 during a tomosynthesis examination in accordance with the prior art. During the examination, the X-ray tube assembly 4 moves, guided by the rotary arm 8, on a circular path continuously along the arrow and radiates with an X-ray beam R onto the object O to be examined on the detector 5. Meanwhile, a plurality of X-ray projections or "X-ray shots" is acquired with the detector 5 during this continuous movement.

As indicated at the central position, during an X-ray projection, which lasts a certain amount of time, the X-ray tube assembly 4 moves along a path a. Here the central position during the X-ray projection is represented in a solid line and start and end positions are represented in dotted lines (the X-ray projection occurs between start and end positions).

An enlargement of the acquired region of the object is shown at the bottom with a demonstration point D. This demonstration point D casts a shadow S on the detector 5, which is then interpreted as a mapping of the demonstration point D.

During the scan, the angle of the X-ray beam R now moves over the region between the dotted lines, and this results in a diffusing of the cast shadow of the demonstration point. This is represented by three shadows S for the three X-ray beams R drawn. In practice, only one long line would be seen.

This movement artifact is prevented by FFS tracking, which keeps the focal point constantly in the central position (indicated by a solid line).

Figure 6:
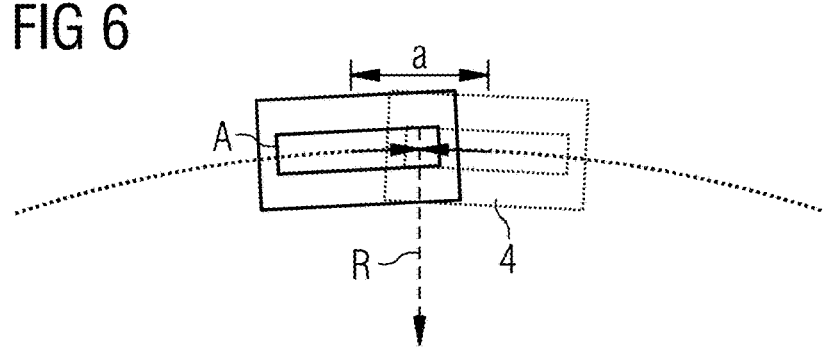
FIG. 6 shows an example of FFS tracking during a tomosynthesis examination according to an example embodiment.

FIG. 6 shows an example of FFS tracking during a tomosynthesis examination. The uppermost point of the circular path is again represented with the start position (in a solid line here) and the end position (dotted) of the X-ray tube assembly 4 in which the anode A is still indicated here. An FFS deflection causes the electron beam E, which impinges from above into the image plane and onto the anode A, to firstly be deflected to the right and subsequently to the left (arrows), so the impingement point on the anode A (focal point) always remains at a position in the room over the entire movement of the X-ray tube assembly 4 during this X-ray projection.

If the result is compared with FIG. 5, then only the X-ray beams R indicated in broken lines would be emitted and no longer the ones in dotted lines. Diffusion (the movement artifact) is prevented as a result.

Unfortunately the FFS tracking is not optimum since the FFS deflection is no longer accurate precisely in the case of large deflections (for example start and end positions as represented) owing to manufacturing tolerances of the FFS deflecting coil 14. One or more example embodiments of the present invention can optimize this FFS deflection by way of calibration, however.

FIG. 7 shows a sequence plan for one possible sequence of an inventive method for calibration and/or for quality control of an FFS X-ray system 1, as is represented for example in FIG. 4.

In step I, the absorption mask M is positioned in the calibration position P between the X-ray tube assembly 4 and the X-ray detector 5 of the FFS X-ray system 1 such that an X-ray beam R from X-ray tube assembly 4 to X-ray detector 5 would run through the absorption mask M.

In step II, the X-ray beam R is switched on with a predefined FFS deflection of an electron beam E in the X-ray tube assembly 4. The absorption mask is mapped on the detector 5 thereby.

In step III, the position of the mapping B of the absorption mask M on the X-ray detector 5 is measured when the X-ray beam R is switched on. In addition, the deflection current IS is ascertained for the FFS deflection.

As indicated by the backward-directed arrow, the measurement according to step II and III is then repeated for a plurality of different FFS deflections. Preferably, measurements with the maximum positive FFS deflection with no FFS deflection and with maximum negative FFS deflection, inter alia, are carried out.

In step IV, a biunique allocation Z of deflection current IS and FFS deflection of the electron beam E is created on the basis of the measured plurality of ascertained deflection currents IS and the respectively measured positions of the mapping B.

In step V, a deflection current IS in accordance with the created allocation Z is applied in the FFS deflecting coil 14 for a predefined FFS deflection. This can occur for an examination as is outlined in FIG. 5.

Figure 8:
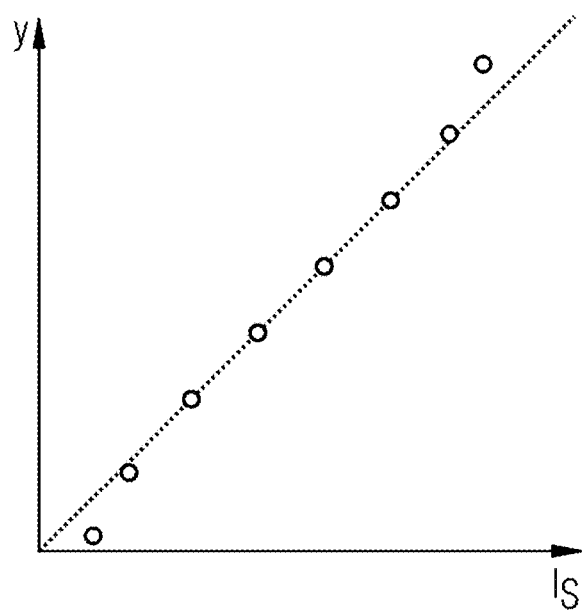
FIG. 8 shows an example of an allocation according to an example embodiment.

FIG. 8 shows an example of an allocation Z as can be created with a method as in FIG. 7. The deflection current IS is plotted on the X-axis, the FFS deflection on the Y-axis. It can be seen that the allocation (measuring points) at the edges with greatest FFS deflection deviate from a proportional plotting (dotted line).

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

To conclude, it is pointed out once again that the method previously described in detail and the represented system are merely exemplary embodiments, which can be modified in a wide variety of ways by a person skilled in the art without departing from the scope of the invention. Furthermore, use of the indefinite article "a" or "an" does not preclude the relevant features from also being present several times. Similarly, terms like "unit" do not preclude the relevant components from comprising a plurality of cooperating sub-components, which can optionally also be spatially distributed.

The invention claimed is:

1. A system for at least one of calibration or quality control of a Flying Focal Spot (FFS) X-ray system, wherein the FFS X-ray system comprises a flat-panel X-ray detector, an X-ray tube assembly with a cathode and an anode and a FFS deflecting coil for FFS deflection of an electron beam between the cathode and the anode in a deflecting direction transverse to a movement of the electron beam, the system comprising:

an absorption mask having an interior and an exterior, wherein the interior and the exterior differ with respect to X-ray absorption and the interior being limited at least in the deflecting direction of the electron beam on both sides of the exterior, the absorption mask being positionable in a calibration position through which an X-ray beam radiates from the X-ray tube assembly to the X-ray detector;

a measuring facility configured to measure at least one position of a mapping of the absorption mask on the X-ray detector when the X-ray beam is switched on;

an allocation unit configured to ascertain a deflection current of the FFS deflecting coil for each measured position of the mapping of the absorption mask on the X-ray detector, and the allocation unit being further configured to create a biunique allocation of the deflection current for the FFS deflection of the electron beam based on each ascertained deflection current and the respectively measured position of the mapping; and a control unit configured for applying a deflection current in the FFS deflecting coil in accordance with at least one of the allocation or for controlling a data stream for storing the allocation for a comparison with earlier allocations.

2. The system of claim 1, wherein the absorption mask is movable between a rest position outside of an intentional beam cone of the X-ray beam and the calibration position.

3. The system of claim 1, wherein the absorption mask is at a collimator or in the collimator of the X-ray tube assembly.

4. The system of claim 1, wherein the absorption mask is at a filter or in the filter of the X-ray tube assembly.

5. The system of claim 1, wherein the absorption mask is attached to a compression plate for a mammography system.

6. The system of claim 1, wherein the absorption mask is a phantom, the absorption mask being arranged upstream of a tube output of the X-ray tube assembly.

7. The system of claim 1, wherein the absorption mask is formed such that
an X-ray-absorbing element is in the interior and the exterior is substantially X-ray-transparent, or
the interior is X-ray-transparent and the exterior is substantially X-ray-absorbing.

8. An FFS X-ray system comprising:
a flat-panel X-ray detector;
an X-ray tube assembly with a cathode and an anode;
an FFS deflecting coil for FFS deflection of an electron beam between the cathode and the anode in a deflecting direction transverse to a movement of the electron beam; and
the system of claim 1.

9. The FFS X-ray system of claim 8, wherein the X-ray tube assembly is an FFS X-ray tube assembly, the FFS X-ray tube assembly including the absorption mask of the system.

10. A control facility for the FFS X-ray system of claim 8, comprising:
the measuring facility;
the allocation unit; and
the control unit.

11. A method for at least one of calibration or quality control of the FFS X-ray system of claim 8, the method comprising:
positioning the absorption mask between the X-ray tube assembly and the X-ray detector of the FFS X-ray system such that the X-ray beam from the X-ray tube assembly to the X-ray detector runs through the absorption mask;
switching-on the X-ray beam with a predefined FFS deflection of the electron beam in the X-ray tube assembly;
measuring the position of the mapping of the absorption mask on the X-ray detector when the X-ray beam is switched on and ascertaining the deflection current for the FFS deflection;
repeating the measurement for a plurality of different FFS deflections; and
creating the biunique allocation of deflection current to FFS deflection of the electron beam, based on the measured plurality of ascertained deflection currents and the respectively measured positions of the mapping.

12. The method of claim 11, wherein a maximum negative FFS deflection with a maximum negative deflection current and a maximum positive FFS deflection with a maximum positive deflection current are defined.

13. The method of claim 11, wherein the measuring measures the position of the mapping of the absorption mask at different energies of the X-ray beam.

14. The method of claim 11, further comprising:
tracking the electron beam using the FFS deflection, wherein the deflection current is applied in the FFS deflecting coil in accordance with the created allocation.

15. The method of claim 11, further comprising:
creating at least one further allocation at different positions of the X-ray tube assembly.

16. The system of claim 2, wherein the absorption mask is at a collimator or in the collimator of the X-ray tube assembly.

17. The system of claim 2, wherein the absorption mask is at a filter or in the filter of the X-ray tube assembly.

18. The system of claim 2, wherein the absorption mask is attached to a compression plate for a mammography system.

19. The system of claim 2, wherein the absorption mask is a phantom, the absorption mask being arranged upstream of a tube output of the X-ray tube assembly.

20. The system of claim 2, wherein the absorption mask is formed such that
an X-ray-absorbing element is in the interior and the exterior is substantially X-ray-transparent, or
the interior is X-ray-transparent and the exterior is substantially X-ray-absorbing.

* * * * *